United States Patent [19]

Nagel

[11] Patent Number: 4,494,557

[45] Date of Patent: Jan. 22, 1985

[54] METHOD OF CONDITIONING HAIR

[76] Inventor: Gerald D. Nagel, 6404 W. North Ave., Wauwatosa, Wis. 53213

[21] Appl. No.: 419,836

[22] Filed: Sep. 20, 1982

[51] Int. Cl.$^3$ .......................... A45D 7/00; A61K 7/09; A61K 7/06
[52] U.S. Cl. ......................................... 132/7; 424/71; 424/70
[58] Field of Search .......................... 424/70, 71; 132/7

[56] References Cited

U.S. PATENT DOCUMENTS

| | | | |
|---|---|---|---|
| 3,958,581 | 5/1976 | Abegg et al. | 132/7 |
| 3,973,574 | 8/1976 | Minagawa et al. | 132/7 |
| 3,981,312 | 9/1976 | Patel | 132/7 |
| 4,303,085 | 12/1981 | de la Guardia et al. | 132/7 |

FOREIGN PATENT DOCUMENTS

| | | | |
|---|---|---|---|
| 49-21070 | 5/1974 | Japan | 424/71 |
| 2066310 | 7/1981 | United Kingdom | 132/7 |

*Primary Examiner*—Sam Rosen
*Assistant Examiner*—Shawn P. Foley
*Attorney, Agent, or Firm*—Andrus, Sceales, Starke & Sawall

[57] ABSTRACT

A method of conditioning human hair to provide a long lasting permanent hair wave includes the step of applying a reforming mixture to the hair after applying a wave solution but before applying a neutralizer solution. The reforming mixture includes magnesium sulfate, water and a hair reconstructor solution with a magnesium sulfate to reconstructor weight ratio within the range of from about 0.7 to 1 to about 2.7 to 1 and a water to reconstructor weight ratio within the range of from about 1 to 1 to about 3.5 to 1.

8 Claims, No Drawings

METHOD OF CONDITIONING HAIR

BACKGROUND OF THE INVENTION

This invention relates to methods of treating human hair, and more particularly to a method of providing a permanent wave in human hair.

Various methods of treating hair with chemicals and heat to produce a permanent hair wave are known to beauticians. As is well known in the art, hair is stretched in the permanent waving process, and fixed into a new "permanent" position with the aid of an alkaline waving solution, curling "rods" and heat. One such method includes first shampooing to clean the hair, sectioning and wrapping the hair on the rods, and then applying the permanent waving solution. Since hair is composed chiefly of elongated epidermal cells covered by a cuticle of flat imbricated cells, the alkalinity of the waving solution aids in opening the hair cuticles so that the sulfur bonds of the cystine linkages which bridge the long peptide chain molecules of the elongated epidermal cells may be broken. Once broken, sufficient altering and rearrangement of the cystine sulfur linkages is capable of producing permanent set in the hair.

The permanent wave solution may be of the endothermic type which requires heat from a hair dryer, the exothermic type which liberates heat after its application, or the "cold wave" type wherein only the body heat from the head is utilized during the treatment. The wave solution is then allowed to remain on the hair for between about 5 to 30 minutes depending upon the type of wave solution. The hair is thus shaped into a desired wave or curl depending upon the size and shape of the rods.

After it has been determined that the hair has accepted the wave, the hair is water rinsed, towel blotted and a neutralizer or acid solution is applied to close the hair cuticles. The hair is then once again water rinsed and the rods are removed. The permanent wave is thus complete and the hair may be styled as desired.

Another method of treating hair to produce a permanent hair wave is described in Volume III, Number 1 of The Nexus Herald published by Nexus Products Company of Santa Barbara, Calif. In this treatment a solution sold under the trade designation EPITOME is applied to the hair after the permanent wave solution has been applied and the curl is complete but before the neutralizer solution is applied. The EPITOME solution, however, makes the hair very brittle so that if a rod or curler is removed or readjusted during this phase of the treatment that portion of the hair may be completely broken off.

It is thus desirable to provide a permanent hair wave treatment that will not cause the hair to become excessively brittle during treatment and will be long lasting.

SUMMARY OF THE INVENTION

A method of conditioning human hair to produce a long lasting permanent hair wave. The method includes the step of applying a reforming mixture to the hair after applying a permanent wave solution but before applying a neutralizer solution.

The reforming mixture includes magnesium sulfate, water and a hair reconstructor solution. The mixture has a magnesium sulfate to reconstructor weight ratio within the range of from about 0.7 to 1 to about 2.7 to 1, and a water to reconstructor weight ratio within the range of about 1 to 1 to about 3.5 to 1.

DESCRIPTION OF THE PREFERRED EMBODIMENT

The present invention comprises a method of conditioning human hair to produce a long lasting permanent hair wave. The method includes the step of applying a reforming mixture to the hair after a permanent wave solution has been applied but before a neutralizer solution has been applied to the hair. The reforming mixture includes a reconstructor solution, magnesium sulfate and water.

The reconstructor solution employed in the reforming mixture is readily available as a raw material from various commercial sources. For example, the Nexus Products Company of Santa Barbara, Calif. sells hair reconstructor solutions under the trade designation KERAPHIX, and LaMaur Inc. of Minneapolis, Minn. sells a reconstructor solution under the trade designation NUCLEIC A. Another source of such reconstructor is Jherimack Enterprises Inc. of Redding, Calif. selling under the trade designation NUTRI-PAK. All of these reconstructor solutions are readily available at beauty salons throughout the United States. The reconstructor solution used in the present invention is thus well known in the art.

KERAPHIX is the preferred reconstructor solution for use in the method of the present invention. The composition of KERAPHIX includes water, hydrolyzed animal protein, keratin, stear-alkonium chloride, glycerin, safflower oil, ceteareth-5, cetyl alcohol, quaternium-19, panthenol, nucleic acids, zinc, magnesium citrate, methylparaben, propylparaben, chamomile extract, fragrances and manganese. The specific weight percentages of these ingredients are not known since they are claimed to be trade secrets by the Nexus Products Company. However, it is known that the above ingredients are listed in amounts of decreasing weight percentages, i.e., water is the largest ingredient while manganese is the smallest ingredient by weight. KERAPHIX is a whitish colored cream which weighs about 28.33 grams per fluid ounce. Preferably, between about ½ fluid ounce and about ¼ fluid ounce or about 14 to about 7 grams of KERAPHIX is utilized in the reforming mixture of the present invention.

The keratin contained in the KERAPHIX reconstructor has the following composition by weight:

Isoleucine: 2.40%
Leucine: 2.54%
Lisine: 3.52%
Methionine: 0.78%
Cystine: 3.20%
Phenylalanine: 2.30%
Thrionine: 9.92%
Tyrosine: 0.78%
Valine: 5.12%
Arginine: 9.00%
Histidine: 1.28%
Alanine: 4.32%
Aspartic Acid: 8.86%
Gentamic Acid: 15.84%
Clycine: 5.52%
Proline: 9.14%
Serine: 12.92%
Tryptophan: 2.26%

The reforming mixture includes magnesium sulfate. Magnesium sulfate is readily available in crystal or powder form and has the following chemical structure: $MgSO_4 \cdot 7H_2O$ Magnesium sulfate is commonly referred to as Epsom or bitter salts. Between about 15.5 grams and about 11.5 grams of magnesium sulfate is utilized in the reforming mixture of the present invention with 15.5 grams being the preferred amount. If an amount greater than about 15.5 grams is utilized, the magnesium sulfate begins to crystallize out after application on the hair which is undesirable. If less than about 11.5 grams is used the solution becomes excessively weak.

The reforming mixture also includes an amount of water which must be added to what is already present in the reconstruction solution. Between about 0.5 fluid ounces (14.7 grams) and about 0.75 fluid ounces (22.1 grams) of water are added in order to thin or dilute the creamy reconstruction solution. This dilution permits the reforming mixture to readily penetrate into the hair. Distilled water is preferably used so that a longer shelf life is provided. However, tap water may also be used if the reforming mixture is to be applied within a short period of time after mixing.

It can thus readily be determined that the reconstructor solution comprises from about 15.7% to about 34.8% by weight of the reforming mixture while the magnesium sulfate comprises from about 24.1% to about 41.6% by weight of the reforming mixture and the water comprises from about 33.2% to about 54.4% by weight of the reforming mixture. Preferably, the reconstructor solution comprises between about 21% to about 27%, the magnesium sulfate comprises between about 30% to about 35%, and the water between about 42% to about 45% by weight of the reforming mixture.

The reforming mixture thus has a magnesium sulfate to reconstructor weight ratio within the range of from about 0.7 to 1 to about 2.7 to 1, and a water to reconstructor weight ratio within the range of from about 1 to 1 to about 3.5 to 1. Preferably, the magnesium sulfate to reconstructor weight ratio is about 1.3 to 1, and the water to reconstructor weight ratio is about 1.8 to 1.

A number of reforming mixtures formulated in accordance with the above description were prepared. In each of the following examples the mixture was blended and shaken in a container until the magnesium sulfate crystals were completely dissolved and that container was sealed and placed in a larger container filled with hot water to warm the mixture to insure thorough mixing. All examples were prepared initially at room temperature.

EXAMPLE 1

| Ingredient | Parts by Weight (grams) |
| --- | --- |
| KERAPHIX (½ oz.) | 14.0 |
| Epsom salts | 11.5 |
| Water (½ oz.) | 14.7 |

EXAMPLE 2

| Ingredient | Parts by Weight (grams) |
| --- | --- |
| KERAPHIX (½ oz.) | 14.0 |
| Epsom salts | 15.5 |
| Water (¾ oz.) | 22.1 |

EXAMPLE 3

| Ingredient | Parts by Weight (grams) |
| --- | --- |
| KERAPHIX (¼ oz.) | 7.0 |
| Epsom salts | 15.5 |
| Water (½ oz.) | 14.7 |

The above sample mixtures provide a sufficient amount for a single application. The above sample mixtures were applied to the hair of separate customers desiring permanent hair waves. The mixtures were applied directly to the hair while the hair was wrapped on the rods after the wave solution had been applied but prior to the application of a neutralizer solution. In particular, after the wave solution had been applied and allowed to progress to curl the hair, the hair was rinsed with mildly hot tap water, then towel blotted to remove any excess moisture, and finally the reforming mixture was applied. The hair was then covered with a plastic cap placed securely over the rods, and then heated under a hair dryer for between about 15 to about 25 minutes to infuse the mixture into the hair. This infusion reconstructs the bonds in the hair for a long lasting permanent wave.

Following the application of the reforming mixture, the hair was uncapped, towel blotted to remove excess moisture, and a neutralizer was applied. Finally, the rods were removed and the hair was rinsed in water and styled to the desired shape.

Various modes of carrying out the invention are contemplated as being within the scope of the following claims particularly pointing out and distinctly claiming the subject matter which is regarded as the invention.

I claim:

1. In a method of conditioning human hair to provide a long lasting permanent wave which includes the steps of applying a permanent wave solution to the hair to shape the hair followed by applying a neutralizer solution to the hair to neutralize the effect of the permanent wave solution and reconstitute the hair, the improvement comprising the steps of:

applying a reforming mixture to the hair after the hair has been shaped but prior to applying the neutralizer solution, said reforming mixture consisting essentially of magnesium sulfate, water and a reconstructor solution and having a magnesium sulfate to reconstructor weight ratio within the range of from about 0.7 to 1 to about 2.7 to 1 and a water to reconstructor weight ratio within the range of from about 1 to 1 to about 3.5 to 1; and heating the hair for between about 15 to about 25 minutes after applying the reforming mixture but prior to applying the neutralizer solution.

2. The method of claim 1, including the further step of covering the hair with a plastic cap prior to heating.

3. The method of claim 1, wherein said reforming mixture is applied while the hair is wrapped and stretched on curling rods.

4. The method of claim 1, including the further step of warming the reforming mixture prior to applying said mixture to the hair.

5. In a method of conditioning human hair to provide a long lasting permanent wave which includes the steps of applying a permanent wave solution to the hair to shape the hair followed by applying a neutralizer solution to the hair to neutralize the effect of the permanent wave solution and reconstitute the hair, the improvement comprising the steps of:

applying a reforming mixture to the hair after the hair has been shaped but prior to applying the neutralizer solution, said reforming mixture consisting essentially of an aqueous solution of magnesium sulfate having between about 24% to about 42% by weight magnesium sulfate; and heating the hair for between about 15 to about 25 minutes after applying the reforming mixture but prior to applying the neutralizer solution.

6. The method of claim 5, including the further step of covering the hair with a plastic cap prior to heating.

7. The method of claim 5, wherein said reforming mixture is applied while the hair is wrapped and stretched on curling rods.

8. The method of claim 5, including the further step of warming the reforming mixture prior to applying said mixture to the hair.

* * * * *